United States Patent
Shang

(10) Patent No.: US 10,463,876 B1
(45) Date of Patent: Nov. 5, 2019

(54) PHOTODYNAMIC THERAPY DIAGNOSTIC DEVICE CAPABLE OF OPTICAL FIBER PUNCTURE

(71) Applicant: Hua Shang, Jiangsu (CN)

(72) Inventor: Hua Shang, Jiangsu (CN)

( * ) Notice: Subject to any disclaimer, the term of this patent is extended or adjusted under 35 U.S.C. 154(b) by 0 days.

(21) Appl. No.: 16/372,989

(22) Filed: Apr. 2, 2019

Related U.S. Application Data

(63) Continuation of application No. PCT/CN2018/097460, filed on Jul. 27, 2018.

(51) Int. Cl.
| | |
|---|---|
| *A61N 5/06* | (2006.01) |
| *A61B 18/22* | (2006.01) |
| *A61N 5/067* | (2006.01) |

(52) U.S. Cl.
CPC .......... *A61N 5/062* (2013.01); *A61N 5/0601* (2013.01); *A61B 2018/2261* (2013.01); *A61N 2005/067* (2013.01); *A61N 2005/0612* (2013.01); *A61N 2005/0658* (2013.01)

(58) Field of Classification Search
CPC .................. A61N 5/0601; A61N 5/062; A61N 2005/0612; A61N 2005/0658; A61N 2005/067; A61B 2018/2261
See application file for complete search history.

(56) References Cited

U.S. PATENT DOCUMENTS

| | | | | |
|---|---|---|---|---|
| 4,336,809 A | * | 6/1982 | Clark .................. | A61B 5/0084 600/478 |
| 5,330,465 A | * | 7/1994 | Doiron .................. | A61B 18/22 606/7 |
| 5,928,222 A | * | 7/1999 | Kleinerman ............. | G01J 5/08 374/E11.017 |

(Continued)

*Primary Examiner* — Christopher A Flory
(74) *Attorney, Agent, or Firm* — Hauptman Ham, LLP

(57) ABSTRACT

This disclosure provides a photodynamic therapy diagnostic device capable of optical fiber puncture. This device comprises an optical fiber, a laser, a spectrocoupler and a fluorescence analyzer; in which the optical fiber comprises a body portion and a puncture needle head, one end of the body portion is connected with the puncture needle head, and the other end is connected with the spectrocoupler; in which the spectrocoupler is connected with the laser and the fluorescence analyzer to enable a laser emitted by the laser to enter the optical fiber via the spectrocoupler, and a fluorescence produced by the photosensitizer after absorbing the laser to enter fluorescence analyzer via the optical fiber and the spectrocoupler. This therapy diagnostic device, the laser emits a laser with a wavelength that can be absorbed by the photosensitive drug; the laser can pass through the spectrocoupler and then pass through the optical fiber needle tubing, so as to reach the tumor site in the body. The red light is absorbed by the photosensitive drug in the tumor to produce singlet oxygen to kill the tumor cells. The photosensitive drug after being excited produces fluorescence which is collected and transmitted by the optical fiber. Then, the fluorescence enters the fluorescence analyzer via the spectrocoupler. Thereby, the fluorescence quantum yield and the therapeutic effect can be obtained by analyzing the related results, achieving the effect of simultaneous treatment and diagnosis.

10 Claims, 7 Drawing Sheets

(56) References Cited

U.S. PATENT DOCUMENTS

| | | | |
|---|---|---|---|
| 2002/0010500 A1* | 1/2002 | Chen | A61N 5/0601 607/89 |
| 2002/0186921 A1* | 12/2002 | Schumacher | G02B 6/0008 385/31 |
| 2004/0202209 A1* | 10/2004 | Huang | A61K 49/0036 372/21 |
| 2006/0189896 A1* | 8/2006 | Davis | A61M 25/0013 600/585 |
| 2007/0100285 A1* | 5/2007 | Griffin | A61M 25/0013 604/164.11 |
| 2007/0260295 A1* | 11/2007 | Chen | A61N 5/0601 607/88 |
| 2008/0019657 A1* | 1/2008 | Maitland | G02B 6/0008 385/140 |
| 2009/0264768 A1* | 10/2009 | Courtney | A61B 5/0062 600/463 |
| 2009/0275933 A1* | 11/2009 | Zelickson | A61B 18/22 606/15 |
| 2011/0009737 A1* | 1/2011 | Manstein | A61B 18/203 600/424 |
| 2012/0089207 A1* | 4/2012 | Chen | A61N 5/0601 607/92 |
| 2013/0150871 A1* | 6/2013 | Belson | A61B 17/00234 606/148 |
| 2013/0261614 A1* | 10/2013 | Appling | A61B 18/24 606/15 |
| 2013/0345556 A1* | 12/2013 | Courtney | A61B 5/0062 600/425 |
| 2014/0336458 A1* | 11/2014 | Belson | A61B 17/00234 600/109 |
| 2017/0224952 A1* | 8/2017 | Barneck | A61M 25/00 |
| 2019/0060612 A1* | 2/2019 | Besselink | A61M 25/0053 |

* cited by examiner

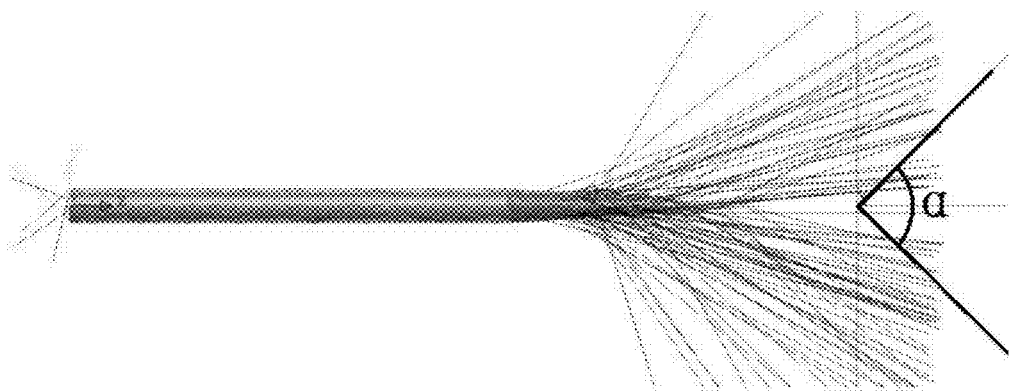
FIG. 23
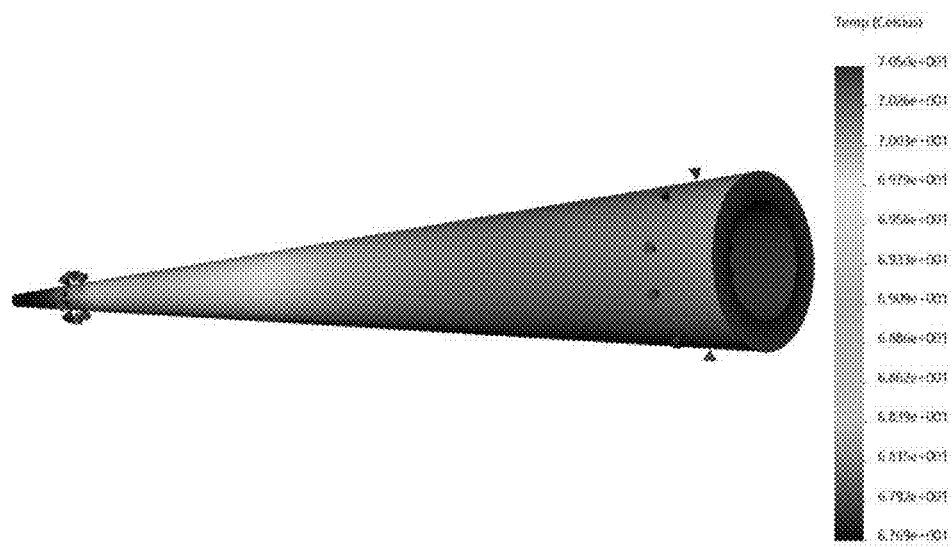
FIG. 24
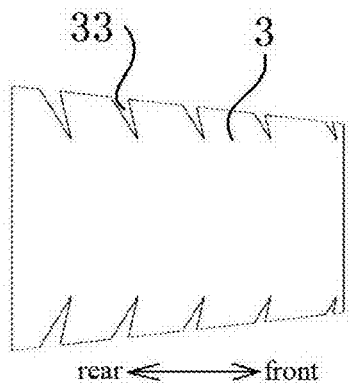 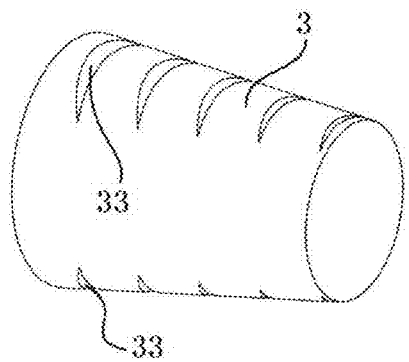
FIG. 25  FIG. 26

PHOTODYNAMIC THERAPY DIAGNOSTIC DEVICE CAPABLE OF OPTICAL FIBER PUNCTURE

PRIORITY CLAIM

The present application is a continuing application of PCT Patent Application No. PCT/CN2018/097460, filed Jul. 27, 2018, which is incorporated herein by reference in its entirety.

TECHNICAL FIELD

The present disclosure relates to the technical field of medical instruments, in particular to a photodynamic therapy diagnostic device capable of optical fiber puncture.

BACKGROUND

Photodynamic Therapy (PDT) is a new technology for the diagnosis and treatment of diseases by using the photodynamic effect. This therapy is based on the photodynamic effect. This is a photosensitization reaction with biological effects in which oxygen molecule is involved. It comprises the following processes: the photosensitizer absorbed by a tissue is excited by the irradiation of a specific wavelength of laser; and then the excited state of the photosensitizer transfers energy to the oxygen in the surrounding environment, to generate a highly active singlet oxygen; singlet oxygen and adjacent biomacromolecules occur oxidation reaction, and thus produce cytotoxicity, which in turn leads to cell damage and even death. Compared with traditional therapies, photodynamic therapy has the advantages of less trauma, good targeting, no drug resistance and side effects. However, since photodynamic therapy mainly uses in the range of more than 600 nm wavelength in the red light region, the light in this region will be lost due to the absorption in a human body. Generally, only the light having the wavelength in few millimeters to several tens of millimeters can be transmitted. For some tumors deep in the body, photodynamic therapy is ineffective. With the aid of optical fiber, endoscopes, and other interventional techniques, the laser can be directed into the deep of body for treatment, avoiding the trauma and pain of surgery such as thoracotomy and laparotomy. Currently, light can be introduced into the body by a puncture needle comprising optical fiber. However, in order to overcome the resistance during puncturing, the optical fiber is wrapped by a hard metal material. Therefore, the needle tubing is thicker. During the process for puncturing, a large pressure is required to perform the puncturing, which is likely to cause a larger trauma and damage to the normal vascular tissue, and bleeding.

Photodynamic therapy produces singlet oxygen to kill tumor cells, in which the fluorescence yield of singlet oxygen is an important indicator of the therapeutic efficacy. Currently, the yield of singlet oxygen is generally determined by analyzing residual fluorescence in the blood, or by analyzing a sample obtained from the puncture, which cannot be able to achieve rapid on-line detection, and has a great impact on the treatment effect and the accuracy of the case studies.

SUMMARY

In view of the above, an object of the present disclosure is to provide a photodynamic therapy diagnostic device capable of optical fiber puncture, so as to solve defects in the prior art.

The object of the present disclosure can be achieved by the following technical solutions.

A photodynamic therapy diagnostic device capable of optical fiber puncture is provided. The photodynamic therapy diagnostic device comprises an optical fiber, a laser, a spectrocoupler and a fluorescence analyzer; in which the optical fiber comprises a body portion and a puncture needle head, one end of the body portion is connected with the puncture needle head, and the other end is connected with the spectrocoupler; in which the spectrocoupler is connected with the laser and the fluorescence analyzer to enable a laser emitted by the laser to enter the optical fiber via the spectrocoupler, and a fluorescence produced by the photosensitizer after absorbing the laser to enter the fluorescence analyzer via the optical fiber and the spectrocoupler; in which the puncture needle head comprises a cylindrical head and a tapered head which is a tapered tail end having a tapered diameter formed by a taper method; the periphery of the body portion is wrapped with a body tube, the cylindrical head is wrapped with a metal casing, and the periphery of the tapered head is wrapped with a needle head cladding layer; one end of the metal casing is fixedly connected with the body tube, and the other end is fixedly connected with the needle head cladding layer; in the needle head cladding layer, the part thereof corresponding to the tapered tail end of the tapered head is provided with a taper structure exactly wrapped around the periphery of tapered tail end and having a tapered diameter.

Further, the metal casing is tightly wrapped around the periphery of the cylindrical head of the optical fiber, to integrally connect the optical fiber with the metal casing; the metal casing has a spiral structure or has inverted kerfs structure on the outer surface thereof.

Further, an end connected with the spectrocoupler of the optical fiber or the body tube is further connected with a drive device capable of vibrating backwards and forwards, in order to apply a forward force to the optic fiber puncture needle while vibrating. Preferably, the drive device is a sonic vibration motor, has 10 μm to 500 μm of amplitude of vibration backwards and forwards, and 10 Hz to 1000 Hz of a vibration frequency.

Further, the needle head cladding layer may be a polymer jacket or a split-shaped needle head made of memory metal; when the needle head cladding layer is the polymer jacket, an inverted-tooth or inverted kerfs structure is provided outside the polymer jacket, so as to have a smaller resistance when advancing, and have a larger resistance when retreating; when the needle head cladding layer is the split-shaped needle head, the split-shaped needle head is composed of a plurality of tapered petals; when the temperature is T0, each of tapered petals in the split-shaped needle head made of memory metal is closed, and the split-shaped needle head after closing exhibits a conical structure, and after closing, the split-shaped needle head is exactly wrapped around the tapered head of optical fiber; when the temperature is T1, each of tapered petals in the split-shaped needle head made of memory metal is opened, and the tapered head of optical fiber is exposed to enable light to direct irradiate onto the tumor.

The present disclosure provides a photodynamic therapy diagnostic device capable of optical fiber puncture; the beneficial effects thereof is mainly in that: (i) In the therapy diagnostic device, the laser of this therapy diagnostic device emits a laser with a wavelength that can be absorbed by the photosensitizer; the laser can pass through the spectrocoupler and then pass through the optical fiber needle tubing, so as to reach the tumor site in the body. The red light is absorbed by the photosensitive drug in the tumor to produce singlet oxygen to kill the tumor cells. The photosensitive drug after being excited produces fluorescence which is collected and transmitted by the optical fiber. Then, the fluorescence enters the fluorescence analyzer via the spectrocoupler. Thereby, the fluorescence quantum yield and the therapeutic effect can be obtained by analyzing the related results, achieving the effect of simultaneous treatment and diagnosis. (ii) Regarding the optical fiber puncture needle tubing, through the synergistic effect with various components thereof, it can be transmitted fast in the long blood vessels, such as being able to smoothly pass through blood vessels up to 2 m long. In addition, a higher light emission efficiency and therapeutic effect can be achieved, thereby having important application value and significance in the treatment of photodynamic tumors. Moreover, the puncture needle tubing also can be applied in other fields, such as eliminating vascular obstructions or performing vascular puncture, etc. (iii) The present disclosure subtly adopts a tapered head with a thinner diameter formed by the taper method which is used as the optical fiber puncture needle head, the effective irradiation rate of light is greatly improved, which is beneficial to the effective cooperation of light and photosensitizer, and reduces the waste of light or photosensitizer, thereby increasing the treatment effect and reducing costs. More importantly, by controlling the specifications of the tapered head, refractive index, the angle of the tapered head or the tapered tail, and the refractive index of polymer jacket, the present disclosure achieves that the light emitted from the tapered head can mainly irradiate to a certain angle in the front. Therefore, the present disclosure can significantly increase the irradiation efficiency and the treatment effect, thereby reducing the waste rate of the light and photosensitizer and increasing the efficiency thereof. (iv) The effective irradiation rate of the light is greatly improved by adopting the taper method to form a tapered head with a tapered diameter and by controlling the taper angle of the tapered head, which is helpful to effectively cooperate with the light irradiation and the photosensitizer, decrease the waste of the light and the photosensitizer, thereby improving the treatment effect and reducing the cost. The cylindrical head may auxiliary irradiate to epitaxial components. The spiral metal casing wrapped around the cylindrical head plays an important role in the flexibility and strength of the puncture needle tubing and the puncture needle head. More importantly, the length, the spiral kerfs, the width of spiral sheet or metal sheet has extremely important auxiliary therapic effect on the photodynamic tumor treatment. That is, a small amount of light can be emitted from the kerfs of the metal casing when the light is emitted from the tapered head, so as to help the tapered head to realize the effective treatment of the whole tumor. (v). The tapered head is finer, which makes it more flexible, less brittleness and less likely to break. The needle head cladding layer can protect the tapered head from breaking easily and from the contamination by complex liquid or solid in the blood vessels. The inverted-tooth structure or the inverted kerf structure on the polymer jacket and/or the metal casing makes the forward resistance smaller and the backward resistance larger, which effectively reduces the thrust required for puncturing, makes the movement of the puncture needle tubing in the blood vessels more smoothly, and reduces the difficulty and time of surgery. The present disclosure is designed with an inverted-tooth structure or inverted kerf structure, and is equipped with a vibration motor, so as to realize an effective transmission which is convenient to advance and not easy to retreat, and is favorable for moving smoothly in the blood vessels. The puncture needle tubing can regularly undergo a slight deformation under the design of the vibration motor. Moreover, the pitch of the spiral part is decreased, thereby helping to move forward in the blood vessels. Meanwhile, the polymer jacket prevents it from retreating and thus increases the transmission effect greatly. (vi). Even if the tapered head is broken, the polymer jacket will still protect the tapered head, so that it will neither damage the blood vessels, nor be lost in the body. The split-shaped needle head subtly adopts the characteristics of the memory metal, and creatively combines with the moving temperature in the body and the thermal effect of light, etc. Thereby, in the transmission process, the present disclosure achieves that the closed split-shaped needle can still perform the puncture while protecting the optical fiber head. It is beneficial to pass across the blood vessels during moving, and thus is more practical. In addition, through the thermal effect of light, the split-shaped needle head is opened during illumination, and the light in the optical fiber can directly irradiate to the target site for treatment.

In summary, the present disclosure has good clinical application effect, high practicability, and a potential value for promotion and application.

BRIEF DESCRIPTION OF THE DRAWINGS

FIG. 23 is diagram illustrating the emission range of light on the tapered head when the split-shaped needle is opened;

FIG. 24 is diagram illustrating the temperature distribution of the split-shaped needle head under light irradiation;

FIG. 25 shows the diagram of the outer surface of the metal casing;

FIG. 26 shows the diagram of the outer surface of the metal casing.

Figure 1:
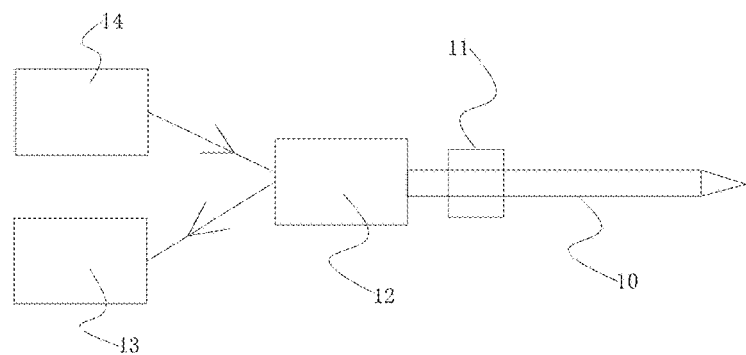
FIG. 1 is a schematic structure diagram of the whole photodynamic therapy diagnostic device.

LIST OF REFERENCE SYMBOLS 1 cylindrical head
2 tapered head
3 polymer jacket
4 metal casing
5 split-shaped needle head
6 needle head cladding layer
8 body portion
9 body tube
10 optical fiber puncture needle tubing
11 vibration motor
12 spectrocoupler
13 fluorescence analyzer
14 laser
21 tapered tail end
31 taper structure
32 inverted-tooth structure
33 inverted-kerf
51 tapered petal
52 annular ring
53 tip end
54 tail end
106 body tube casing
107 hydrophilic coating

DETAILED DESCRIPTION

Various examples of the present disclosure are described below for details. Apparently, the described examples are only a part of examples in the present disclosure, rather than all of them. While the following contains many specific implementation details, they should not be construed as limitations on the scope of any claims, but rather as descriptions to particular examples. Based on the examples provided by the disclosure, other examples obtained by those skilled in the art without creative efforts are encompassed in the scope of the disclosure.

Example 1

A photodynamic therapy diagnostic device capable of optical fiber puncture is provided. The photodynamic therapy diagnostic device comprises an optical fiber puncture needle tubing 10, a laser 14, a spectrocoupler 12 and a fluorescence analyzer 13; in which the optical fiber puncture needle tubing comprises an optical fiber comprising a body portion 8 and a puncture needle head, one end of the body portion 8 is connected with the puncture needle head, and the other end is connected with the spectrocoupler 12; in which the spectrocoupler 12 is connected with the laser 14 and the fluorescence analyzer 13 to enable a laser emitted by the laser 14 to enter the optical fiber via the spectrocoupler 12, and a fluorescence produced by the photosensitizer after absorbing the laser to enter the fluorescence analyzer 13 via the optical fiber and the spectrocoupler 12, as shown in FIG. 1.

The puncture needle head comprises a cylindrical head 1 and a tapered head 2. The forefront end or the free end of the tapered head 2 is a tapered tail end having a tapered diameter formed by a taper method. One end of the cylindrical head 1 is fixedly or integrally connected to the body portion 8 or integrally shaped with the body portion 8, the other end is fixedly or integrally connected with the end having a larger diameter of the tapered head, or they are integrally shaped.

Figure 3:
FIG. 3 is a cross-sectional diagram of the optical fiber puncture needle tubing.

The periphery of the body portion 8 is wrapped with a body tube 9, and the cylindrical head 1 is wrapped with a metal casing 4. The metal casing 4 wraps around the periphery of the cylindrical head 1 tightly, to integrate the cylindrical head 1 of the optical fiber with the metal casing 4. The periphery of tapered head 2 is wrapped with a needle head cladding layer 6. One end of the metal casing 4 is fixedly or integrally connected with the needle head cladding layer, and the other end of the metal casing is fixedly or integrally connected with the body tube. As shown in FIG. 3, the puncture needle head of optical fiber and the metal casing 4 outside the puncture needle head and the polymer jacket 3 can be collectively referred to as a puncture needle head end.

Figure 4:
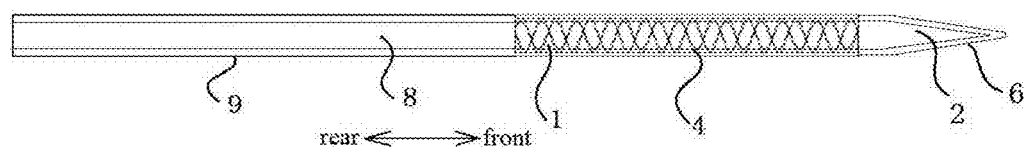
FIG. 4 is a perspective structure diagram of the optical fiber puncture needle tubing.

In the needle cladding layer 6, the part corresponding to the tapered tail end of the tapered head 2 is provided with a taper structure just wrapped around the tapered tail end and having a tapered diameter, as shown in FIGS. 3-4.

Figure 2:
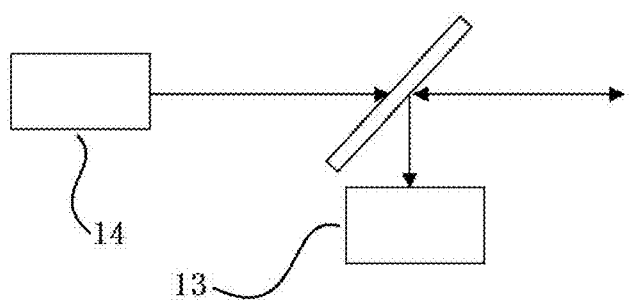
FIG. 2 is a perspective structure diagram of the spectrocoupler.

Preferably, the spectrocoupler 12 is composed of a reflector having a 50% of reflectivity. The red light emitted by the laser 14 passes through the reflector, enters the optical fiber. The fluorescence collected by the optical fiber is reflected by the reflector and then enters the fluorescence analyzer 13, as shown in FIG. 2.

As a further preferred embodiment, the needle head cladding layer is a polymer jacket or a split-shaped needle head made of memory metal.

If the needle head cladding layer is the polymer jacket, the polymer jacket 3 is transparent. In the polymer jacket, the part corresponding to the tapered tail end is provided with a taper structure exactly wrapped around the tapered tail end and having the tapered diameter. In addition, the polymer jacket is provided with an inverted-tooth structure or an inverted kerf structure, so as to have a smaller resistance when advancing, and have a larger resistance when retreating.

When the needle head cladding layer is the split-shaped needle, the split-shaped needle head is composed of a plurality of tapered petals. When the temperature is T0, each of tapered petals in the split-shaped needle head made of memory metal is closed, and the split-shaped needle head after closing exhibits a conical structure, and after closing, the split-shaped needle head is exactly wrapped around the tapered head of optical fiber; when the temperature is T1, each of tapered petals in the split-shaped needle head made of memory metal is opened, and the tapered head of optical fiber is exposed to enable light to directly irradiate onto the tumor. The memory metal comprises nickel-titanium alloy, copper-nickel alloy, copper-aluminum alloy, copper-zinc alloy, etc.

Figure 5:
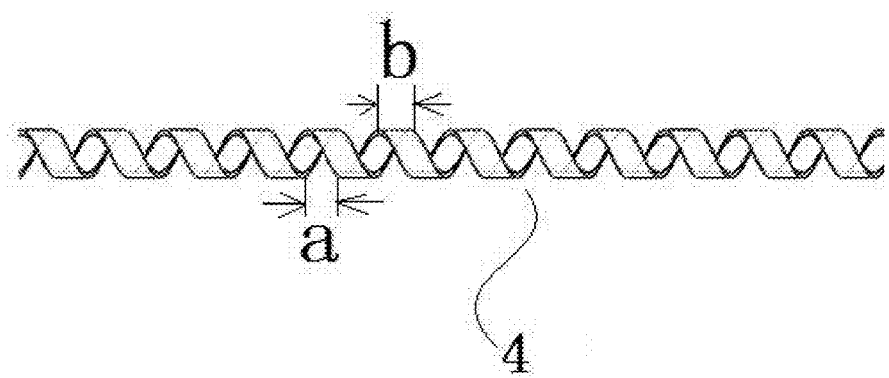
FIG. 5 is a schematic structure diagram of the metal casing.

As a further preferred embodiment, as shown in FIGS. 3-5, the metal casing 4 is a spiral metal casing. The metal casing 4 has a spiral structure having spiral kerfs formed on a metal tube by laser cutting, so that it has a certain strength while increasing a certain flexibility.

More preferably, in the metal casing 4, as shown in FIG. 5, the width a of the kerf is 0.1 to 0.5 mm, such as 0.1 mm, 0.2 mm, 0.3 mm, 0.4 mm, 0.5 mm etc., and the width b of the metal sheet for making the spiral structure of the metal casing 4 is 0.2 to 1 mm, such as 0.2 mm, 0.4 mm, 0.6 mm, 0.8 mm, 1 mm, etc. The values of the kerf width a and the metal spiral sheet width b, as well as the cooperation thereof directly affect the ability to pass through the blood vessels and the smoothness of passing through the blood vessels, and also affect the puncture strength from one blood vessel to another. Width a and width b that are too wider and too narrow will affect its flexibility and strength. If the strength is too high, it cannot pass through the curvature of the blood vessel, and the damage to the inner wall of the blood vessel will be serious; if the flexibility is too high, it cannot pass through the blood vessel having a longer length, especially, when the length of blood vessels to be passed through is within 1 m, it may pass through such blood vessel relatively easier, while when the length beyond 1 m, it will be difficult for the structure to pass through such blood vessels. In addition, it is not easy for the user to control the strength and direction through the handheld end. When piercing and entering another blood vessel from one blood vessel, a lower strength will lead to the inability to pierce the blood vessel. Therefore, when the strength is too high or the flexibility is too high, the device cannot reach blood vessels or organs buried inside the body in a certain depth, such as liver tumors. A good effect can only be achieved upon the suitable width a and suitable width b.

As a further preferred embodiment, an end connected with the spectrocoupler 12 of the optical fiber puncture needle tubing, i.e., the end left outside the body is connected with a drive device capable of vibrating backwards and forwards, in order to apply a forward force to the optic fiber puncture needle tubing while vibrating.

Preferably, the drive device is a sonic vibration motor 11, i.e., vibration motor 11 has 10 μm to 500 μm of amplitude of vibration backwards and forwards, and 10 Hz to 1000 Hz of a vibration frequency.

Figure 6:
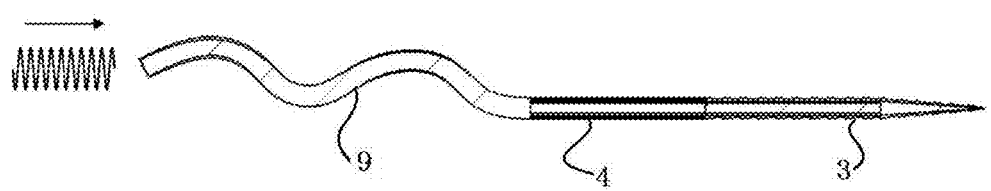
FIG. 6 is a schematic structure diagram of the optical fiber puncture needle tubing during the movement under the drive of the vibration motor.
Figure 7:
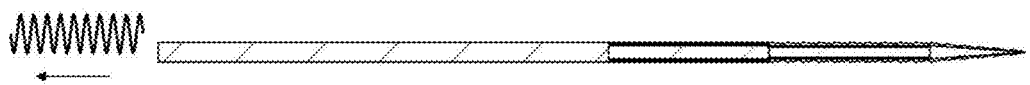
FIG. 7 is another schematic structure diagram of the optical fiber puncture needle tubing during the movement under the drive of the vibration motor.
Figure 8:
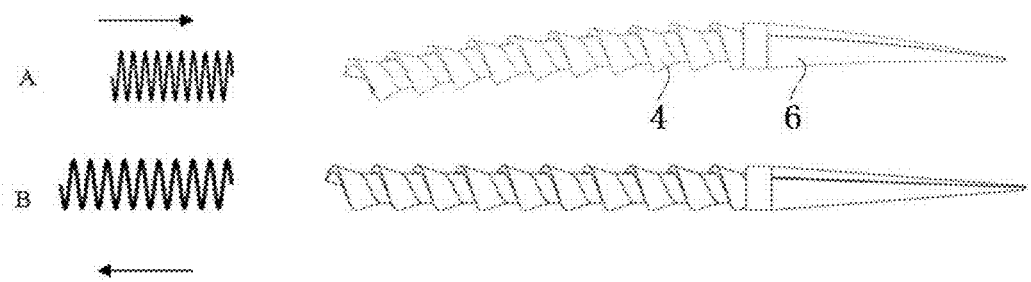
FIG. 8 is a schematic diagram of the structural deformation of the puncture needle head under the drive of the vibration motor.

For example, when puncturing, the puncture needle tubing is connected with the sonic vibration motor 11 which has 100 Hz of the vibration frequency and 50 μm of the vibration amplitude. As shown in FIGS. 6-8, when the sonic vibration motor 11 vibrates forward, the whole structure of the puncture needle tubing is deformed to conduct the vibration. As shown in FIG. 6 and A in FIG. 8, the puncture needle is slightly deformed when vibrating forward. The deformation includes the bending of the puncture needle tubing and the shrinkage in the pitch of the metal casing 4. Such elastic deformation causes the tip of the needle to move forward and overcome the resistance, so as to achieve the forward puncture. When vibrating backward, as shown in FIG. 7 and B in FIG. 8, since the polymer jacket 3 has the inverted-tooth structure, the friction is much greater than the forward movement, the puncture needle tubing is pulled and moved forward as whole, but the tip of the needle may stay still when the sonic vibration motor 11 vibrates backward. The puncture needle tubing continues to puncture forward under the effect of multiple vibrations while applying additional force. This means of puncturing requires less force than the conventional puncture needle, thus allowing the optical fiber puncture needle to be finer and softer, and at the same time capable of completing the puncture effect.

As a further preferred embodiment, the length of the puncture needle head is 7 to 10 mm, in which the length L of the needle head cladding layer is 2.5 to 4 mm, such as 3 mm. The length 1 of the metal casing 4 or the cylindrical head 1 is 4.5 to 6 mm, such as 5 mm; as shown in FIG. 3. If the length of needle head cladding layer 3 or tapered head 2 is too long, it will be easy to cause damage to blood vessels, and will be difficult to move at the slight bend of blood vessels. If too short, the puncturing effect will not be achieved. In addition, it is also impossible to move smoothly and fast in blood vessels with the cooperation of vibration motor 11. If the metal casing 4 is too long or too short, it is neither helpful for moving in blood vessels, or can achieve good auxiliary effect on the puncturing blood vessel walls by tapered head 2. More importantly, the spiral kerfs of the metal casing 4 may emit out a certain light, so as to achieve the auxiliary therapy. Therefore, the width of kerf in the metal casing 4 and the width of the metal sheet, the length of the metal casing 4 play an important role in the therapeutic effect. Therefore, only when the length is suitable, it can pass through the blood vessels smoothly and achieve good transmission, puncturing, thereby having a synergistic effect on the puncture needle tubing.

As a further preferred embodiment, the length of the body tube 9 is 1 to 2 m, such as 1.8 m. The length of the body tube 9 is the same as that of the body portion 8 of the optical fiber. The body tube 8 is tightly wrapped around the body portion 8 of the optical fiber, so that they can be integrated together for easy transmission.

The body portion 8 and the cylindrical head 1 of the optical fiber may have a diameter of 400 μm, which may be a quartz fiber. In the tapered head, the diameter at the foremost end of the tapered tail end is 10 to 50 μm, such as 20 μm, 30 μm, 40 μm. Such fineness can increase the flexibility and reduce the brittleness thereof. The metal casing 4 and the body tube 9 may have an outer diameter of 600 μm and an inner diameter of 400 μm.

Figure 14:
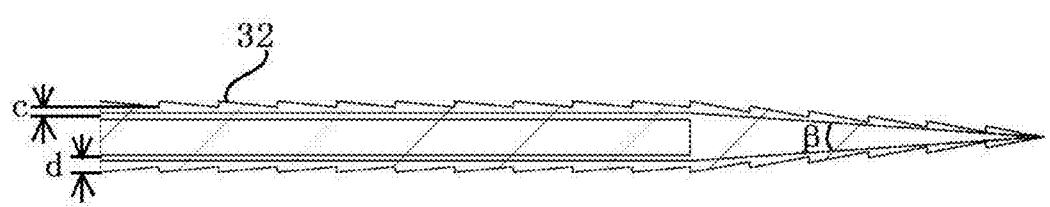
FIG. 14 is a schematic diagram illustrating the thickness of the polymer jacket.
Figure 15:
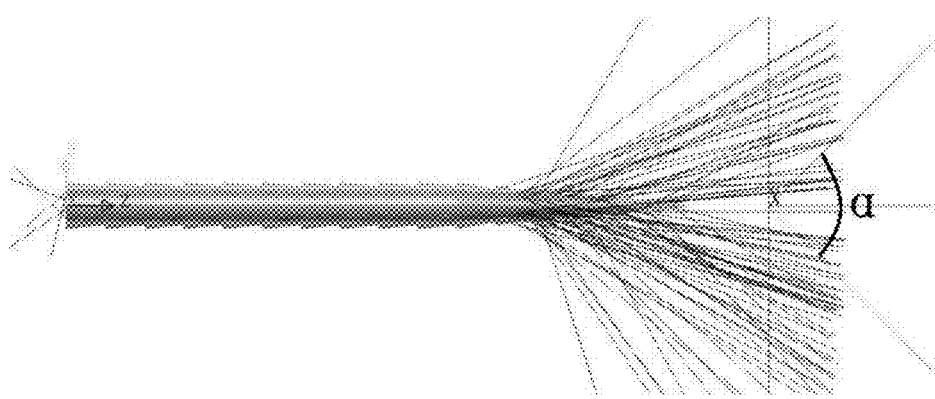
FIG. 15 is diagram illustrating the emission range of light on the tapered head or the polymer jacket.
Figure 19:
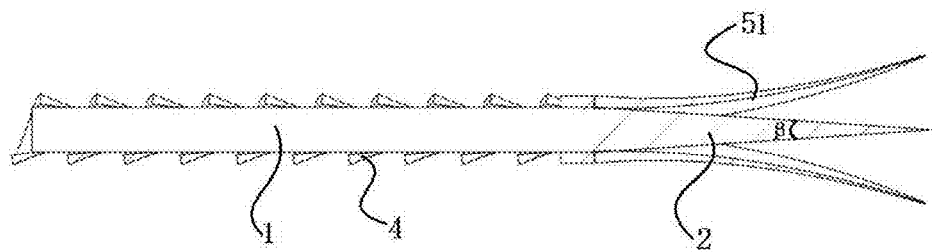
FIG. 19 is a sectional diagram of the puncture needle head of the optical fiber puncture needle tubing, in which the puncture needle head comprises a jacket.

Preferably, the refractive index of the tapered head 2 is 1.45 to 1.55, preferably 1.5. And the taper angle β of the tapered head 2 is 7 to 25°, which can substantially ensure that the light from the tapered head is in the range of 60 to 120, as shown in FIGS. 14 and 19. The angle of which is indicated by α in FIG. 23, or is indicated by α in FIGS. 15 and 23. Specifically, through an optical simulation, it can be known that if the taper angle β is 22°, then the divergence angle α of the light is within 120°; and if the taper angle β is 7.6°, the divergence angle α of the light is within 60°. Therefore, when the taper angle β of the tapered head 2 is 7 to 25°, the light on the tapered head can be efficiently directed to the target position, such as a tumor containing a photosensitizer, so as to effectively utilize the light energy and greatly increase the light output rate. If the puncture cladding layer is the polymer jacket 3, the refractive index of the polymer jacket 3 may be 1.45 to 1.55, such as 1.45, 1.5, 1.55, so as to ensure the light of the tapered head can be emitted from the polymer jacket 3.

The refractive index of the body portion of the optical fiber may be also 1.5. However, the outside of the body portion 8 is coated with a cladding layer having a refractive index, such as 1.2, 1.3, etc., lower than that of the optical fiber, so that the light in the body portion 8 of the optical fiber does not exit from the body portion, restricting the light. Therefore, light can only be emitted from the tapered head, and then directly irradiates onto the tumor containing the photosensitizer.

Preferably, the optical fiber at the spiral metal casing 4, i.e., the cylindrical head 1 of the optical fiber at the kerfs of the spiral casing does not provide with a cladding layer, or has a cladding layer with the refractive index slightly smaller than that of the cylindrical head 1 of the optical fiber. Then, a part of the light can be emitted from the kerfs of the spiral casing, so as to irradiate the other auxiliary parts. Therefore, the key part can be directly irradiated by the tapered head for effective irradiation, and meanwhile the cylindrical head 1 assists the irradiation of the epitaxial part, thereby realizing effective irradiation of the whole part to be irradiated. Irradiation of tumor tissue containing a photosensitizer can effectively increase the efficacy of the photosensitizer and ultimately increase its therapeutic effect.

In this example, the polymer jacket 3 has poor restriction to light, and the refractive index thereof is 1.2 to 1.5, so that the light from the tapered head can pass through the polymer jacket 3. When using, the end of the puncture needle head first pierces into the blood vessel and then transmits in the blood vessel. The end left outside of the body of the puncture needle tubing can be connected to the vibration motor 11, so as to assist the puncture needle head reaching a predetermined site, such as a tumor in the body (e.g., liver tumors) via the blood vessel. Then, the laser 14 is turned on, the red light having 650 nm wavelength (the red light having such wavelength can react the photosensitizer to treat the tumor) enters the optical fiber via the spector coupler 12, and then passes through the tapered head, and finally irradiate to the tumor site containing the photosensitizer. The red light having 650 nm wavelength can produce singlet oxygen after being absorbed by the photosensitive drug (such as PHOTOFRINR) to kill the tumor cells. In addition, the photosensitive drug produces fluorescence after absorbing the red light. The fluorescence collected by the fiber puncture needle passes through the spectrocouple 12 and enters the biofluorescence analyzer 13 (for example, consisting of a monochromator and a highly sensitive detector). The singlet oxygen yield can be determined by analyzing the fluorescence intensity. Through the above device, online fluorescence analysis can be simultaneously performed in photodynamic therapy, which improves the speed and accuracy of the analysis.

Example 2

On the basis of example 1, the body tube 9 is a spiral tube containing a plurality of spiral coils, and the spiral tube has a spiral structure with spiral kerfs formed by laser cutting.

Figure 9:
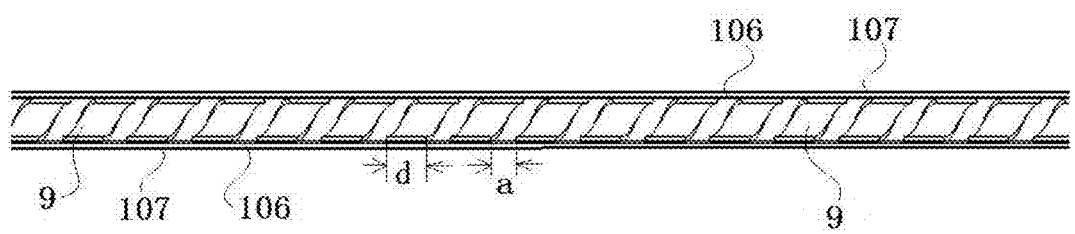
FIG. 9 is a section diagram of the structure of the body tube (viewing from the center to the outside)

As shown in FIG. 9, it shows a cross-section of the body tube 9, viewing from center to the outside. In the body tube 9, the width a of the kerf is 0.02 to 0.2 mm, such as 0.05 mm, 0.08 mm, 0.1 mm 0.15 mm, etc., the width d of the spiral sheet for making the spiral structure in the body tube 9 is 0.5 to 3 mm, such as 1 mm, and the thickness thereof is 0.05 to 0.1 mm, such as 0.08 mm. The length of the body tube 9 is nearly 2 m, and usually 1 to 1.8 m thereof will enter the human body. In addition, the human blood vessels have different thicknesses and a certain degree of curvature. As the blood vessels to be passed through are so long, and the environment are so specific, there are highly requirement for its strength and flexibility. The values of the kerf width a and the spiral sheet width d, as well as the cooperation thereof directly affect the ability to pass through the blood vessels and the smoothness of passing through the blood vessels, and even affect the strength of the puncture needle puncturing the tumor blood vessel walls. The width a and width d that are too wider or too narrow will affect the flexibility and strength. A good effect can only be achieved upon the suitable width a and suitable width d.

The body tube 9 is made of a biomedical metal material including but not limited to one of stainless steel, synthetic fiber, carbon fiber, titanium alloy, gold, silver, etc., preferably stainless steel. As a whole, the body tube is composed of one winding wire (may be two or more winding wires) wrapped around the periphery of body portion 8 of the optical fiber and made of the stainless steel actually.

Figure 10:
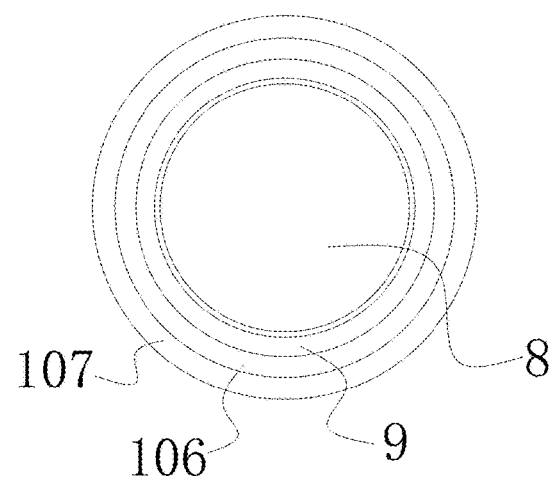
FIG. 10 is a cross-sectional diagram illustrating the body tube wrapped outside the body portion of the optical fiber.

As shown in FIGS. 9-10, a body tube casing 106 is provided outside of the body tube 9, to increase the sealing of the body tube 9 and reduce the resistance; the material of the body tube casing 106 may be polyamide or polypropylene, etc., and other polymers may be acceptable. A hydrophilic coating 107 is provided outside of the body tube casing 106, to increase blood compatibility. The hydrophilic coating 107 is made of a chemically stable material including but not limited to, polytetrafluoroethylene, silicone rubber, polyethylene, polyvinyl chloride, fluorocarbon polymers, and polyurethane. The hydrophilic coating is applied to reduce the resistance in the blood vessel and to pass through the long blood vessels with complex internal environment.

The hydrophilic coating 107 in this example may be replaced with a hydrophobic coating.

Example 3

On the basis of example 1 or 2, as shown in FIGS. 17-20, the metal sheet for making the spiral metal casing 4 has an inverted-tooth structure, such structure has a smaller resistance when advancing and a larger resistance, so that it can be puncturing in a progressive manner under the applied sight impact, and thus can effectively reduce the force required for puncturing.

The inverted-tooth structure is such that the metal sheet 41 for making the metal casing 4 has a thickness of the front end smaller than that of the rear end, to make the optical fiber puncture needle advancing easier and retreating tough.

Figure 20:
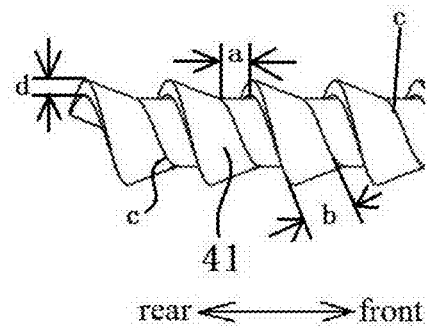
FIG. 20 is a sectional diagram of a part of the spiral metal casing.

More preferably, as shown in FIG. 20, since the thickness c of the front end of the metal sheet is too thin, the thickness thereof is not easily indicated in this figure, so that only the position of c is indicated, and the thickness relationship is not provided. In the inverted-tooth structure of the metal casing 4, i.e., the structure in which the thickness of the front end of the metal sheet for making the metal casing is smaller than that of the rear end, the thickness c of the front end of the metal sheet is 50 to 70 μm, the thickness d of the rear end of the metal sheet is 90 to 110 μm, and the difference in thickness between the front end and the rear end is 30 to 50 μm. Controlling thickness is quite important for effective and smooth transmission and advancement. If the thickness difference is too large, it either needs to increase the outer diameter of the metal casing, or needs to reduce the inner diameter of the metal casing, which has a greater influence on the overall puncture needle tubing. In addition, if the thickness difference is too large, the thickness of the back side of the metal sheet will be increased greatly, which in turn increases the resistance during advancing. Moreover, for the small or fine blood vessels, it will increase the degree of damage to the inner wall of the blood vessels. If the thickness difference is too small, it cannot play the role of assisting advancement and preventing retreating.

Example 4

On the basis of any of the examples 1-3, as shown in FIGS. 11-14, if the needle head cladding layer is the polymer jacket, the outside corresponding to the tapered tail end 21 of the optical fiber in the polymer jacket 3 is designed with a taper structure 31 with a tapered diameter, which is consistent with the structure of the tapered tail end 21 of the tapered head 2.

The polymer jacket 3 may be formed by polyamide or polypropylene. The polymer jacket 3 is provided with an inverted-tooth structure or an inverted kerf structure, as shown in FIGS. 11-14. Such structure has a small resistance when advancing and a larger resistance when retreating, so that it can puncture in a progressive manner under the applied sight impact, and can effectively reduce the force required for puncturing.

Figure 11:
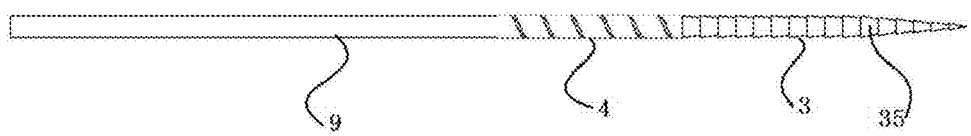
FIG. 11 is a schematic structure diagram of the whole optical fiber puncture needle tubing.
Figure 12:
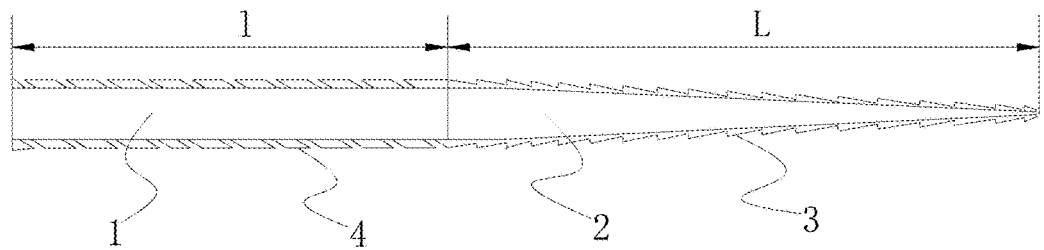
FIG. 12 is a sectional diagram of the puncture needle head comprising the jacket.
Figure 13:
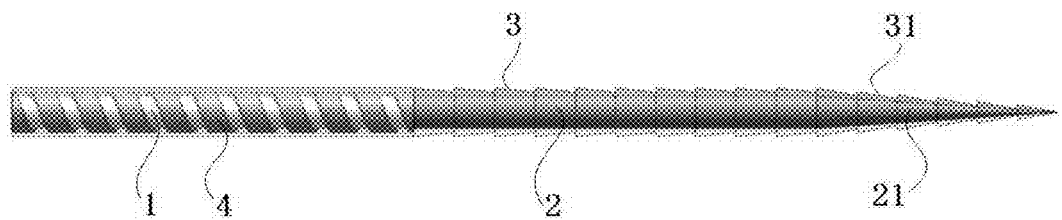
FIG. 13 is a perspective structure diagram of the puncture needle head comprising the jacket.

As a further preferred embodiment, the inverted-tooth structure 32 of the polymer jacket 3 is formed by a plurality of frustule structures with a small front-end diameter and a large rear-end diameter, i.e., the plurality of frustule structure are arranged on the periphery of the tapered head by end to end, so as to make the fiber puncture needle tubing easier to move forward and not easy to retreat, as shown in FIG. 11.

Specifically, as shown in FIG. 5, in the inverted-tooth structure 32, the thickness c of the front end of the frustule structure is 50 to 70 μm, and the thickness d of the rear end of the frustule structure is 90 to 110 μm, and the difference in the thickness between the front end and the rear end is 30 to 50 μm. Controlling thickness is quite important for effective and smooth transmission and advancement. If the thickness difference is too large, it either needs to increase the outer diameter of the metal casing, or needs to reduce the inner diameter of the metal casing, which has a greater influence on the overall puncture needle tubing. In addition, if the thickness difference is too large, the thickness of the back side of the frustule will be increased greatly, which in turn increases the resistance during advancing. Moreover, for the small or fine blood vessels, it will increase the degree of damage to the inner wall of the blood vessels. If the thickness difference is too small, it will not play the role of assisting advancement and preventing retreating. Therefore, the thickness of the inverted-tooth structure 32 and the difference in thickness between the front end and the rear end of the frustule have important influence on the advance of the optical fiber puncture needle tubing.

Figure 16:
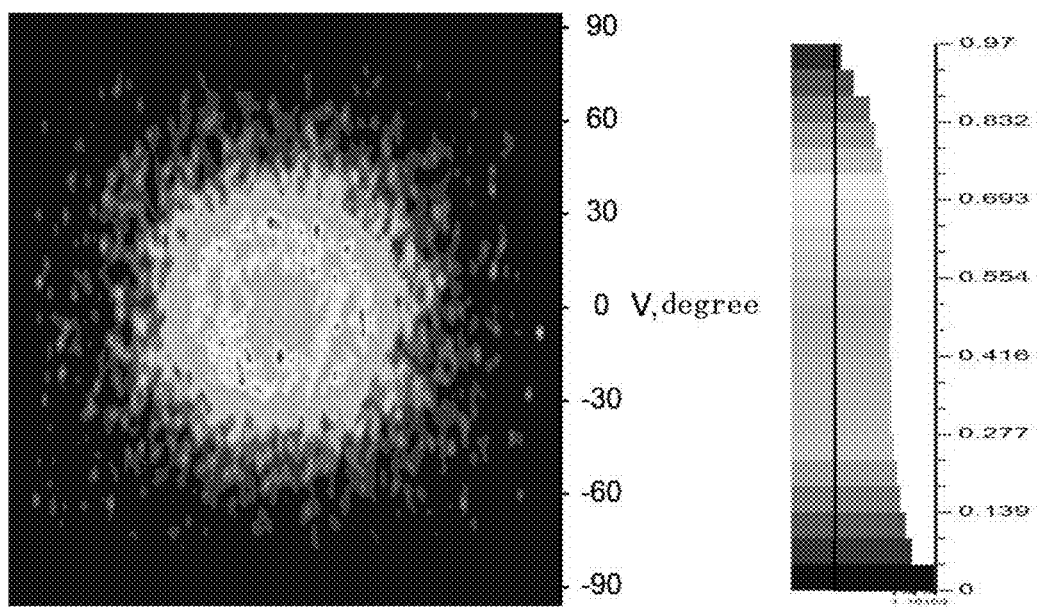
FIG. 16 is diagram illustrating the exit spot of the tapered head.

In this example, if the input optical fiber has a wavelength of 650 nm, when the input power is 1 W, the output rate of the light output from the optical fiber tapered head is 0.94 W, the output power is high. In addition, the divergence angle thereof is about 60°, which can effectively irradiate or treat the key parts. The shape of the spot is shown in FIG. 16.

Example 5

Figure 17:
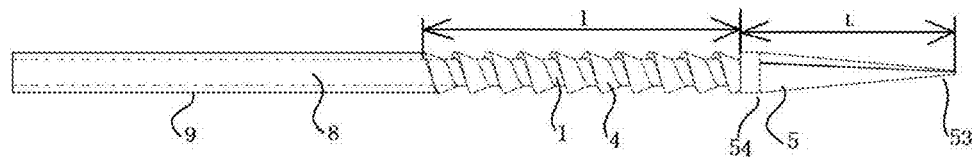
FIG. 17 is a schematic diagram of the optical fiber puncture needle tubing when the split-shaped needle is closed.
Figure 18:
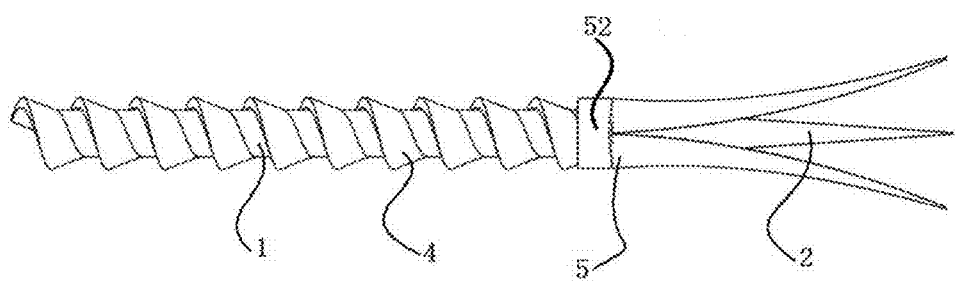
FIG. 18 is a schematic diagram of the structure of the head end when the split-shaped needle is opened.

On the basis of example 3, as shown in FIGS. 17-19, if the needle head cladding layer is the split-shaped needle head 5 made of memory metal, the split-shaped needle head can be deformed to the opened state, with the increasing of the temperature due to light illumination, so that light of the optical fiber can be emitted out. The metal casing 4 is fixedly connected to the tail end or the end having large diameter end of the split-shaped needle head 5. The split-shaped needle head 5 is composed of a plurality of tapered petals 51, as shown in FIG. 19.

When the temperature is T0, as shown in FIG. 17, each of tapered petals 51 in the split-shaped needle head 5 made of memory metal is closed, and the split-shaped needle head 5 after closing exhibits a conical structure, and after closing, the split-shaped needle head 5 is exactly wrapped around the tapered head 2 of optical fiber. The optical fiber is wrapped in the split-shaped structure to protect the optical fiber, and the conical split-shaped structure can conveniently move in the blood vessels during the passage through the blood vessels. In other words, the moving is smooth, i.e., when advancing, the resistance is smaller, while retreating, the resistance is larger.

When the temperature is T1, as shown in FIGS. 18-19, each of tapered petals 51 in the split-shaped needle head 5 made of memory metal is opened, and the tapered head 2 of optical fiber is exposed to enable light to directly irradiate onto the tumor.

As a further preferred embodiment, when no light is emitted from the optical fiber, i.e., when the laser 14 is not turned on, the temperature of the split-shaped needle head transmitted in the body is T0, each of tapered petals in the split-shaped needle head is closed to form a needle-shaped structure or a conical structure. When the optical fiber emits light, i.e., the laser 14 connected to the optical fiber is turned on to transmit the light to the optical fiber, the light is emitted by the tapered optical fiber and irradiate on the memory metal, the temperature of the split-shaped needle head 5 made of memory metal is gradually increased to T1 due to the thermal effect of the optical fiber. Then, each of tapered petals in the split-shaped needle head is opened, i.e., when exceeding phase transition temperature, the outward prefabricated deformation is produced to exhibit the opened state. Light exits through the opening, that is, the tapered head of the optical fiber is exposed to enable light to directly emit from the opened split-shaped needle head.

The temperature T0 may be 37° C., and the temperature T1 may be 50° C. For example, at the temperature T0 (for example, 37° C.), the split-shaped needle head 5 is prefabricated into the closed shape, and at the temperature T1 (for example, 50° C.), the split-shaped needle head 5 is prefabricated into the opened shape. When puncturing in the body, no light passes through the optical fiber, and the temperature of the split-shaped needle head 5 in the head portion is the body temperature T0 (37° C.). The transmission and puncturing can be realized as the split-shaped needle head 5 is closed. After reaching a predetermined site, a 100 mW laser with a wavelength of 650 nm passes through the optical fiber, and radiates to the split-shaped needle head 5 made of memory metal through the tapered head of the optical fiber. As shown in FIG. 24, it shows the outside of the puncture needle head having a 500 W/(m2·K) convection heat conduction (typical heat dissipation rate of liquid convection), in which the temperature of the needle head can be raised to 70.5° C. under the 100 mW laser, and when exceeding T1 temperature (50° C.), the needle head is deformed to the opened state.

As a further preferred embodiment, the tapered petals 51 have the same curvature at each point and are formed by arc-shaped surfaces. All of the tapered petals 51 are identical in terms of shape and size, so that the forces distributed on the tapered petals 51 are more uniform, and the strength thereof is greater. The split-shaped structure comprises 2 to 5 tapered petals, preferably 2 tapered petals or 3 tapered petals. If the number of tapered petals is too large, each of tapered petals will be too small, thereby not having sufficient strength.

Preferably, the thickness of the split-shaped needle head 5 or the tapered petals 51 is 0.06 to 0.12 mm. When it is closed, it is exactly wrapped around the outside of the tapered head 2. Preferably, there is no gap between the tapered head 2 and the split-shaped needle head. In addition, the tapered head 2 has an effect of assisting the improvement of strength of the split-shaped needle head 5; and it can combine with the tapered petals 51 having a certain thickness, to facilitate the transmission and piercing of the puncture needle tubing, which brings out a synergistic effect.

Preferably, the split-shaped needle head 5 includes a tail end 54 and a tip end 53, as shown in FIGS. 17-18. The tapered petal 51 is gradually decreased from the tail end to the tip end. When each of tapered petals 51 is closed, the diameter of the tail end 54 is larger than that of the tip end 53; the tail ends of the tapered petals are integrally connected to form an annular ring 52 of the annular structure, and the annular ring 52 is fixedly connected to the metal casing 4.

Preferably, when each of tapered petals 51 is closed, two adjacent sides in the two adjacent tapered petals 51 are closely abutted, and the split-shaped structure constitutes a fully enclosed conical structure, thereby better protecting the tapered head of the optical fiber. As if the tapered head is polluted during the transmission process, it will affect the irradiation rate of light, and thus affects the action of the photosensitizer on the tumor site.

Example 6

Figure 21:
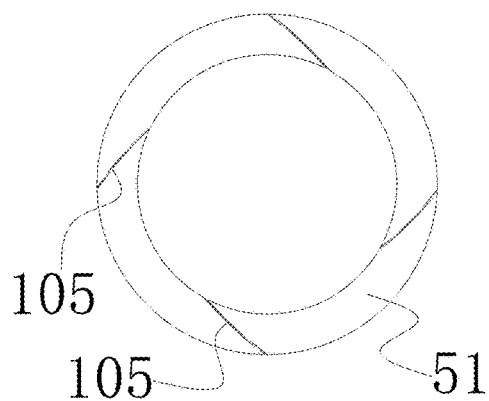
FIG. 21 is a cross-sectional diagram illustrating the structure that the split-shaped needle head is closed together.
Figure 22:
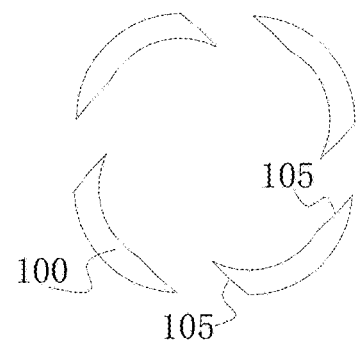
FIG. 22 is a cross-sectional diagram illustrating the structure that the split-shaped needle head is opened.

On the basis of example 5, as shown in FIGS. 21-22, in the tapered petals 51, the sides for abutting or separating from the adjacent tapered petals are inclined faces 105. That is, one tapered petal 51 has two sides, each of which has a beveled configuration. And all the inclined faces 105 of the tapered petals 51 are consistent in direction (i.e., in the clockwise or counterclockwise direction), which ensures that the two abutted inclined faces in two adjacent tapered petals can be exactly fitted together. That is, one is gradually inclined outward from the inside, while the other is inclined inward from the outside, and thus the two can be just fitted together, so that the inner and the outer surfaces after being fitted together are smooth arced surfaces.

The design of the beveled configuration means that the width of the sides is widened, so that the contact area is increased when the two adjacent tapered petals 51 are abutting each other, and the bonding strength is greater between tapered petals 51 after the split-shaped needle head 5 is closed, obtaining a better puncture effect of the needle-shaped structure. More importantly, since the sides are designed as inclined faces 105, the contact width is increased when the two adjacent tapered petals 51 are abutting each other, obtain a better sealing. Therefore, during the transmission in the blood vessels, it is not easy to cause the inner optical fiber tapered head 2 to be infected, thereby affecting the final emitting of the light.

The figure for this example takes four tapered petals 51 as the example. But two or three tapered petals also can be used.

Example 7

On the basis of example 5 or 6, in the tapered petals 51, the side or inclined face 105 for abutting or separating from the adjacent tapered petals 51 is provided with a first flexible layer, to make the abutment strength between the tapered petals 51 more tight and the sealing therebetween better. The better sealing can prevent the tapered head from the fluid contamination in the blood vessels better, while helping to increase the strength of the closed split-shaped needle head.

As a further preferred embodiment, the inner side surface of the tip end of the tapered petal is provided with a second flexible layer, to make when the split-shaped structure is closed, the abutment strength between the tapered petals more tight and the sealing therebetween better.

The first and second flexible layers may have a thickness of 0.005 to 0.04 mm, and the materials of the first and second flexible layers may be polytetrafluoroethylene, polyamide or polypropylene or the like.

Example 8

On the basis of any of the examples 1-7, the polymer jacket 3 may have a structure that the outer surface thereof is designed with a plurality of inverted kerfs 33, as shown in FIGS. 25-26. That is, the inverted kerfs 33 are formed on the outer surface of a metal tube in the shape of wedge by laser cutting, and the inverted kerfs 33 are inclined backward, as shown in FIG. 25. The width of the inverted kerf 33 decreases gradually from the outside to the inside end, and the thickness thereof also decreases gradually. Preferably, the polymer jacket 3 in this example may have a structure with tapered diameter from the rear to the front end, which is convenient for advancing, as shown in FIGS. 25-26.

The inverted kerf structure makes the forward resistance smaller and the backward resistance larger, which effectively reduces the thrust required for puncturing, makes the movement of the puncture needle tubing smoother in the blood vessels, and reduces the difficulty and time of surgery.

It should be noted that the inverted-tooth structure of the metal casing in example 5 may also be the inverted kerf structure as described in this example.

Example 9

The present discloses relates to the use of the photodynamic therapy diagnostic device capable of optical fiber puncture. The puncture needle tubing can be used in the smooth movement in the long blood vessels, the effective puncture of blood vessel wall or intravascular obstruction, and the irradiation of the blood vessels, tissue or organ deep in human body. Therefore, such puncturing needle tubing can be effectively used in dredge of obstructions in blood vessels and in the dredge or treatment of congestion or clots in tissues. More importantly, the therapeutic diagnosis of the corresponding disease can also be achieved by guiding light from the body into the fluorescence analyzer 13 for analysis.

If the optical fiber puncture needle tubing is used in photodynamic tumor treatment and the interventional treatment is used for a liver tumor, the optical fiber puncture needle tubing pierces into the femoral artery, then pierces into the liver artery from the femoral artery under the cooperation with the vibration motor 11, and finally enters the blood vessel of the liver tumor. Then, the laser 14 is turned on, the red light emitted by the laser 14 enters the optical fiber via the spectrocoupler 12. Therefore, the light reaches the tapered head at the end of the optical fiber, and then irradiates on the tumor which has been injected a photosensitive drug (if it is the polymer jacket, the light will be directly emitted from the polymer jacket; if it is the split-shaped needle head, the light will be directly emitted from the tapered head when the split-shaped needle is opened), so that the photosensitive drug in the tumor produces singlet oxygen by the photochemical reaction, to cause necrosis and apoptosis of the tumor. Thereby the purpose of treating tumors can be achieved. The fluorescence produced by the photosensitive drug after being excited is collected by the puncture needle head. Then, the fluorescence can pass through the spectroscope and enter into the fluorescence analyzer 13. Therefore, the fluorescence quantum yield and the therapeutic effect will be analyzed by the results of the fluorescence analyzer 13.

Example 10

In order to further study the practical effect of the optical fiber puncture needle tubing in this disclosure, the applicant has carried out the study from various aspects, such as the type and length of the blood vessels to be passed through, the passing time, the damage to the blood vessel, the strength of the tip, irradiation effect, treatment efficiency and the accuracy, and so on.
Method:
taking the biopsy for liver tumor sampling as an example, through the Seldinger arterial puncture technique, under the guidance of radiography, the optical fiber puncture needle tubing enters the hepatic artery through the femoral artery, then enters the hepatic blood vessels through the hepatic artery, and finally enters the tumor blood vessels, under the auxiliary of the vibration motor 11. Then, irradiation and treatment of tumor which has been added photosensitizer are performed.

The length of the blood vessel passed through: 1.6 m.

The puncture needle tubing of examples 2, 4, 5, and 7 are tested as the experimental groups 1-4 respectively.

Comparative Example 1: this comparative example is performed in the same manner as in example 4, except that there is no polymer jacket. Comparative Example 2: this comparative example is performed in the same manner as in example 2, except that there is no the structure of tapered head, no needle head cladding layer. In addition, the forefront of the puncture needle tubing has the structure of the cylindrical head 1 wrapped by the metal casing 4. Comparative Example 3: this comparative example is performed in the same manner as in example 2, except that there is no spiral metal casing 4. That is, the tapered head directly connects with the body portion 8. Comparative Example 4: the body tube of example 2 is changed to a spring. Comparative Example 5: the metal casing 4 of example 2 is changed to a spring. Comparative Example 6: this comparative example is performed in the same manner as in example 5, except that there is no split-shaped needle head, and the tapered head is exposed.

The results of the above examples are summarized in the table below.

|  | Time to reach tumor blood vessels/min | Output efficiency of the optical fiber | Irradiation efficiency of the optical fiber | Tip strength when puncturing/ |
|---|---|---|---|---|
| Experimental group 1 | 4-10 | 95% | 94% | 2.6N |
| Experimental group 2 | 4-10 | 97% | 96% | 2.6N |
| Experimental group 3 | 4-10 | 98% | 95% | 2.7N |
| Experimental group 4 | 4-10 | 99% | 98% | 2.7N |
| Com. ex.1 | 20-30 | 77% | 75% | 2.0N |
| Com. ex 2 | 20-35 | 81% | 53% | — |
| Com. ex 3 | 5-15 | 88% | 60% | 2.4N |
| Com. ex 4 | 20-35 | 88% | 87% | 1.8N |
| Com. ex 5 | 5-15 | 88% | 89% | 1.9N |
| Com. ex 6 | 10-15 | 78% | 73% | 2.0N |

In the above table, i) the time to reach the tumor blood vessels refers to the time required to move in the blood vessels before reaching the tumor tissue. ii) the output efficiency of the optical fiber refers to the percentage of light actually irradiated to the photosensitizer in the tumor and the light from the puncture needle theoretically irradiated to the photosensitizer in the tumor. iii) the irradiation efficiency of the optical fiber refers to the effective amount of light irradiated on the photosensitizer in the tumor, which is in positive ratio with the absorption efficiency of the photosensitizer; iv) the tip strength when puncturing refers to the force of the puncture needle when puncturing the inner wall of the tumor blood vessels.

The results of the above experimental and comparative groups are explained as follows:

Experimental groups 1-4: the structure can move in the blood vessels smoothly; and the outputting rate of light, the irradiation efficiency of the optical fiber, the puncture effect and the therapeutic effect are all better.

Comparative Example 1: Because there is neither polymer jacket nor inverted tooth structure, the moving time in the blood vessels is greatly increased. In addition, since the tapered head is exposed, it has certain brittleness. Therefore, it needs to be careful when moving, and thus affects the moving time in the blood vessels. Because the tapered head is exposed, the endovascular environment has a certain influence on it during the transmission process. In addition, some substances that can affect the refractive index and luminance of light may easy adhere to the tapered head during the process of moving, which leads to the light output efficiency of the optical fiber at the target position is low. Due to its low light output efficiency, it greatly affects the irradiation efficiency of the optical fiber. That is, the light irradiated on the photosensitized is decreased. The force at the tip when puncturing is decreased obviously.

Comparative Example 2: the puncture cannot be performed during moving, which would affect the moving. Because some sites need to pass through a blood vessels by piercing another blood vessel wall, it needs to combine with other means, which greatly affects the total time of moving. The total light output efficiency is low. In addition, the light is only emitted from the top end of the optical fiber and the kerfs of the spiral casing, which greatly reduces the amount of the illumination. In the meantime, there is more blindness, the light emitted cannot be effectively utilized, which reduces the illumination efficiency of the optical fiber and greatly their treatment efficiency. Moreover, because there is no tip end, the piercing cannot be achieved.

Comparative Example 3: as there is no metal casing 4 having the spiral structure, the light is only emitted from the tapered head, the irradiation thereof is only spread over a small area, and specifically only can spread over some important parts; there is almost no light that can irradiate other auxiliary parts. Therefore, it greatly affects the irradiation efficiency, and thus greatly affects their treatment efficiency. In addition, it also influences on the strength of the tip and the moving time in a certain degree.

Comparative Example 4: it is difficult to control the strength and direction of spring, which greatly affects the total moving time. Since the strength thereof also cannot be controlled well, the puncturing effect at a certain point is significantly reduced.

Comparative Example 5: if the selected spring is consistent with the spiral casing in the strength, the flexibility and elasticity thereof are different from those of the spiral casing of the present disclosure. In addition, the direction thereof is not easy to control, resulting in the tip shows less strength than the experimental groups on the whole.

Comparative Example 6: Because the tapered head is exposed, it has certain brittleness. Therefore, it needs to be careful when moving, and thus affects moving. Because the tapered head is exposed, the endovascular environment has a certain influence on it during the transmission process. In addition, some substances that can affect the refractive index and luminance of light may easy adhere to the tapered head during the process of moving, which leads to the light output efficiency of the optical fiber at the target position is low. Due to its low light output efficiency, it greatly affects the irradiation efficiency of the optical fiber. That is, the light irradiated on the photosensitizer is decreased. The force at the tip when puncturing is decreased obviously.

Example 11

A rat tumor model was established. Rats having substantially the same tumor size were taken as the experimental object. In the control, only photosensitizer was applied for treatment. In the experimental group, photosensitizer was applied and the method of the present disclosure was used for illumination.

In the experimental groups 1-3 is irradiated by red light through the optical fiber puncture needle tubing described in examples 2, 4 and 5. The control groups 1-3 correspond to comparative groups 1-3 in example 10, and the method of laser irradiation thereof is consistent with that of experimental groups.

Method: ten days after treatment, the rats were dissected. And, the coronal incision was made according to the puncture point on the surface of rats. Tumor size was vertically and horizontally measured. Tumor volume=$a^2bII/6$ (a is a short diameter of the tumor, and b is a long diameter of the tumor). The tumor growth inhibition rate=[(average volume of tumor in the control group−average volume of the tumor in the experimental group/average volume of the tumor in the control group)]×100%. The obtained inhibition rate of the tumor growth is shown as below.

|  | experimental group 1 | experimental group 2 | experimental group 3 | control group 1 | control group 2 | control group 3 |
|---|---|---|---|---|---|---|
| the inhibition rate of the tumor growth | 80.21% | 83.52% | 86.34% | 62.76% | 60.51% | 49.97% |

Therefore, in the treatment of photodynamic tumor, the efficiency of light emission and illumination has a direct impact on the final treatment effect. The treatment effect of the experimental group is significantly higher than that of the control group.

In the present disclosure, the spectrocoupler is 50:50 plate beam splitter, purchased from Thorlabs. Of course, it also can be purchased from other Manufacturers.

The above description is only a preferred embodiment of the present disclosure, and is not intended to limit the present disclosure. It should be appreciated that various modifications and changes can be made to the present disclosure. Any modifications, equivalents, improvements, etc. made within the spirit and scope of the present disclosure are intended to be included within the scope of the present disclosure.

The invention claimed is:

1. A photodynamic therapy diagnostic device capable of optical fiber puncture, wherein the photodynamic therapy diagnostic device comprises an optical fiber, a laser, a spectrocoupler and a fluorescence analyzer; wherein the optical fiber comprises a body portion and a puncture needle head, one end of the body portion is connected with the puncture needle head, and the other end of the body portion is connected with the spectrocoupler; wherein the spectrocoupler is connected with the laser and the fluorescence analyzer to enable a laser emitted by the laser to enter the optical fiber via the spectrocoupler, and a fluorescence produced by a photosensitizer after absorbing the laser to enter the fluorescence analyzer via the optical fiber and the spectrocoupler; wherein the puncture needle head comprises a cylindrical head and a tapered head which is a tapered tail end having a tapered diameter formed by a taper method; the periphery of the body portion is wrapped with a body tube, the cylindrical head is wrapped with a metal casing, and the periphery of the tapered head is wrapped with a needle head cladding layer; one end of the metal casing is fixedly connected with the body tube, and the other end is fixedly connected with the needle head cladding layer; wherein in the needle head cladding layer, the part thereof corresponding to the tapered tail end of the tapered head is provided with a taper structure exactly wrapped around the tapered tail end and having a tapered diameter.

2. The photodynamic therapy diagnostic device capable of optical fiber puncture according to claim 1, wherein the metal casing is tightly wrapped around the periphery of the cylindrical head of the optical fiber, to integrally connect the optical fiber with the metal casing; the metal casing has a spiral structure or has inverted kerfs structure on the outer surface thereof; if it is the spiral metal casing, the metal casing has a spiral structure with spiral kerfs formed on a metal tube by laser cutting, so that it has a certain strength while increasing a certain flexibility.

3. The photodynamic therapy diagnostic device capable of optical fiber puncture according to claim 2, wherein in the spiral metal casing, a metal sheet for making the metal casing has an inverted tooth structure having a thickness of the front end smaller than that of the rear end, to make the optical fiber puncture needle advancing easier and retreating tough.

4. The photodynamic therapy diagnostic device capable of optical fiber puncture according to claim 2, wherein the body tube is a spiral tube including a plurality of spiral coils, the kerfs of the spiral tube is a taper structure of the spiral kerfs formed by laser cutting; the length of the body tube is 1 to 2 m;
 wherein the length of the puncture needle head is 7 to 10 mm, and the length of the needle cladding head layer is 2.5 to 4 mm; the length of the metal casing is 4.5 to 6 mm;
 in the metal casing, the width a of the kerf is 0.1 to 0.5 mm, the width of the metal sheet for making the spiral structure of the metal casing is 0.2 to 1 mm;
 in the body tube, the width of the kerf is 0.02 to 0.2 mm, the width of the spiral sheet for making the spiral structure in the body tube is 0.5 to 3 mm, the thickness of the body tube is 0.05 to 0.1 mm.

5. The photodynamic therapy diagnostic device capable of optical fiber puncture according to claim 1, wherein an end connected with the spectrocoupler, of the optical fiber or the body tube is further connected with a drive device capable of vibrating backwards and forwards, in order to apply a forward force to the optic fiber puncture needle while vibrating.

6. The photodynamic therapy diagnostic device capable of optical fiber puncture according to claim 5, wherein the drive device is a sonic vibration motor, has 10 μm to 500 μm of amplitude of vibration backwards and forwards, and 10 Hz to 1000 Hz of a vibration frequency.

7. The photodynamic therapy diagnostic device capable of optical fiber puncture according to claim 5, wherein the needle head cladding layer is a polymer jacket;

when the needle head cladding layer is the polymer jacket, a part corresponding the tapered tail end in the polymer jacket is provided with a taper structure exactly wrapped around the periphery of the tapered tail end and having a tapered diameter, the polymer jacket is provided with inverted-tooth or inverted kerfs structure, so as to have a smaller resistance when advancing, and have a larger resistance when retreating.

8. The photodynamic therapy diagnostic device capable of optical fiber puncture according to claim 7, wherein the outside of the body portion of the optical fiber is coated with a body portion cladding layer for preventing the light from being emitted from the side surface of the optical fiber; wherein the taper angle β of the tapered head is 7 to 25°; the refractive index of the tapered head is 1.45 to 1.55;

when the needle head cladding layer is the polymer jacket, the refractive index thereof is 1.4 to 1.55;

the refractive index of the cylindrical head at the kerfs of the metal casing is 1.4 to 1.55, so that a part of light can be emitted from the kerfs of the spiral metal casing;

in the tapered head, the diameter at the foremost end of the tapered tail end is 10 to 50 μm.

9. The photodynamic therapy diagnostic device capable of optical fiber puncture according to claim 7, wherein the inverted-tooth structure of the polymer jacket is formed by a plurality of frustule structures with a small front-end diameter and a large rear-end diameter, so as to make the fiber puncture needle tubing easier to move forward and not easy to retreat;

the inverted kerfs outside the polymer jacket are formed on the outer surface of a metal tube in the shape of wedge by laser cutting, and the inverted kerf is inclined backward, the width of the inverted kerf decreases gradually from the outside to the inside end.

10. The photodynamic therapy diagnostic device capable of optical fiber puncture according to claim 9, wherein in the inverted-tooth structure of the polymer jacket, the thickness of the front end of the frustule structure is 50 to 70 μm, and the thickness of the rear end of the frustule structure is 90 to 110 μm, and the difference in the thickness between the front end and the rear end is 30 to 50 μm.

* * * * *